United States Patent
Mertens et al.

(10) Patent No.: US 11,028,454 B2
(45) Date of Patent: Jun. 8, 2021

(54) INCORPORATION OF THERMO-RESISTANT AND/OR PRESSURE-RESISTANT ORGANISMS IN MATERIALS

(75) Inventors: Johan Mertens, Wetteren (BE); Lynda Beladjal, Wetteren (BE); Frank Devlieghere, Oostkamp (BE); Sam Verbrugghe, Oostakker (BE); Benedikt Sas, Stekene (BE); Filip Du Prez, Ghent (BE); Tom Anthierens, Bruges (BE); Assia Ouchchen, Lokeren (BE)

(73) Assignee: Resilux, Wetteren (BE)

( * ) Notice: Subject to any disclaimer, the term of this patent is extended or adjusted under 35 U.S.C. 154(b) by 0 days.

(21) Appl. No.: 13/120,908

(22) PCT Filed: Sep. 24, 2009

(86) PCT No.: PCT/EP2009/062389
§ 371 (c)(1),
(2), (4) Date: May 26, 2011

(87) PCT Pub. No.: WO2010/034776
PCT Pub. Date: Apr. 1, 2010

(65) Prior Publication Data
US 2011/0217758 A1  Sep. 8, 2011

Related U.S. Application Data

(60) Provisional application No. 61/194,158, filed on Sep. 24, 2008.

(30) Foreign Application Priority Data

Aug. 26, 2009  (EP) ..................................... 09168652

(51) Int. Cl.
*C12N 11/08* (2020.01)
*C12R 1/07* (2006.01)
(52) U.S. Cl.
CPC ................ *C12R 1/07* (2013.01); *C12N 11/08* (2013.01)
(58) Field of Classification Search
None
See application file for complete search history.

(56) References Cited

U.S. PATENT DOCUMENTS

| 5,132,211 | A  | * | 7/1992  | Lundin et al. ................... 435/31 |
| 6,248,321 | B1 | * | 6/2001  | Winder et al. ............... 424/93.5 |
| 6,689,390 | B2 | * | 2/2004  | Bernstein ............. A61K 9/1617 424/484 |
| 7,157,258 | B2 | * | 1/2007  | Durand et al. ................. 435/177 |
| 2003/0165472 | A1 | * | 9/2003 | McGrath et al. ............. 424/93.4 |
| 2004/0175407 | A1 | * | 9/2004 | McDaniel ....................... 424/423 |
| 2005/0084532 | A1 | * | 4/2005 | Howdle et al. ................. 424/486 |
| 2005/0271846 | A1 | * | 12/2005 | Suzuki ......................... 428/36.91 |
| 2007/0068072 | A1 | * | 3/2007 | Xavier et al. ................... 47/57.6 |
| 2007/0207190 | A1 | * | 9/2007 | Dierickx et al. .............. 424/443 |
| 2008/0057047 | A1 | * | 3/2008 | Sas et al. .................. 424/93.462 |

FOREIGN PATENT DOCUMENTS

WO  WO-2006/024115 A1  3/2006

OTHER PUBLICATIONS

Friedberg, Brief. Bioinformatics, 7: 225-242 (2006).*
Thorton et al., Nature Structural Biology, structural genomics supplement, pp. 991-994 (2000).*
Ananta et al., Inn. Food Sci. Emerg. Techol., 2:261-272 (2001).*
Margosch etal (App. Env. Microbiol., 72(5):3476-3481 (2006).*
Nakayama et al., App. Env. Microbiol., 62(10):3897-3900 (1996).*
de Heij et al., Food Tech., 57(3)37-41 2003.*
Loncar et al., Biores. Technol., 147:177-183 (2013).*
Anthierens et al., Inn. Food Sci. Emerg. Techol., 12:594-599 (2011).*
Polymer Data Handbook, Oxford (1999).*
Database Geneseq [Online] EBI; Jun. 30, 2005 (Jun. 30, 2005), "Bacillus amyloliquefaciens KTG0202" XP002554221 retrieved from EBI Database accession No. AEA79493 97% identity with Seq ID 1.
Database Geneseq Jan. 29, 2002 (Jan. 29, 2002), "Bacillus amyloliquefaciens gyrA partial sequence" XP002554222 retrieved from EBI Database accession No. ADM80449 96% identity with Seq ID 1.
Agthe, O. et al., "Untersuchungen zum Uberleben von Sporen von Bacillus Stearorthemophilus beim Spritzglessen von Polyathylen = Investigations on the survival of spores of Bacillus stearothermophilus during moulding of polyethylene with an injection-moulding machine," Archiv Fuer Lebensmittelhygiene—Archives of Meat, Fish and Diary Science, Alfeld, DE, vol. 47, No. 2, May 29, 1996 (May 29, 1996), pp. 40-42.
Konig, Christiane et al., "Autosterilization of biodegradable implants by injection molding process," Journal of Biomedical Materials Research, vol. 38, No. 2, 1997, pp. 115-119.

* cited by examiner

*Primary Examiner* — Thomas J. Visone
(74) *Attorney, Agent, or Firm* — James Creighton Wray

(57) ABSTRACT

The present application relates to methods for producing materials having viable micro-organisms incorporated therein. More particularly, the materials are produced under high temperature and/or high pressure conditions, and the micro-organisms are incorporated in the material before or during these conditions. Also provided are micro-organisms that remain viable under these conditions and have different applications, depending on the nature of the material.

21 Claims, 3 Drawing Sheets
Specification includes a Sequence Listing.

INCORPORATION OF THERMO-RESISTANT AND/OR PRESSURE-RESISTANT ORGANISMS IN MATERIALS

This application is the National Phase Under 35 U.S.C. § 371 of PCT International Application No. PCT/EP2009/062389 which has an International filing date of Sep. 24, 2009, which claims priority to U.S. Provisional Application No. 61/194,158 filed on Sep. 24, 2008 and European Patent Office Application No. EP 09168652.7 filed on Aug. 26, 2009. The entire contents of all applications listed above are hereby incorporated by reference.

FIELD OF THE INVENTION

The present application relates to methods for producing materials having viable micro-organisms incorporated therein. More particularly, the materials (e.g. polymers, plastics, foodstuffs, pharmaceutical preparations) are produced under high temperature and/or high pressure conditions (e.g. extrusion, pelletizing), and the micro-organisms are incorporated in the material before or during these conditions. Also provided are micro-organisms that remain viable under these conditions and have different applications (e.g. as probiotic, or to create an oxygen barrier), typically depending on the nature of the material.

BACKGROUND

The various beneficial properties of many micro-organisms have been recognized for a long time. Typical examples include oxygen consumption or absorption, absorption of radiant energy (e.g. UV absorption) or their use as probiotics. However, incorporating micro-organisms in materials to be able to integrate these beneficial properties in a material is not straightforward. Indeed, many materials, such as polymers, resins, but also foodstuffs, animal feed and even pharmaceutical preparations and drugs, are prepared under conditions of increased temperature, increased pressure or both.

For instance, the processing temperature of permanent, non-biodegradable polymers is well above 100° C., which even at normal pressure conditions, is too high for the incorporation of living material. The implantation of living, active micro-organisms at temperatures of this level is impossible without fatal consequences for these organisms. Thus, even if the organisms which are introduced would normally perform useful activity at normal ambient temperatures, if incorporation of living or viable organisms during the production of the material is not achievable, no benefit can be obtained. This is not only true for polymers and plastics, but also for materials for human and animal consumption (e.g. food or drugs). While the temperatures at which these materials are processed may not necessarily be as high (although they can be), these materials often undergo high-pressure processes such as food extrusion, cooking extrusion, other extrusion processes (e.g. as described in US 20050238721), pelletizing, pressure-cooking, molding, thermo-forming or the like. These high-pressure processes, often combined with high temperatures (and possibly desiccation), are also detrimental of the viability of typical micro-organisms. For instance, Biourge and co-workers tried to include a Bacillus strain (CIP 5832) in dog food and concluded that the extrusion-expansion and drying process resulted thus in the loss of >99% of the spores, and that Bacillus CIP 5832 should thus not be included in the diet before the extrusion-expansion and drying process (Biourge et al., 1998).

Several solutions have been proposed in the art to circumvent this problem. One strategy is not to use micro-organisms, but compounds fulfilling the same function. For instance, U.S. Pat. No. 5,034,252 describes the use of an activating metal into a plastic container for its oxygen barrier properties. While this achieves a similar effect, the use of metals inherently poses more severe biodegradability and environmental issues than micro-organisms. Also, this may make the process more expensive.

An alternative strategy is the separation of the high-pressure (and/or high temperature) step and the mixing of the micro-organisms in the material, typically by applying a coating layer with bacteria on the extruded or pelleted product. In WO2007/60539, a method for the preparation of animal feed is provided in which dead probiotic bacteria are coated onto extruded or pelletised pellets and the coated pellets are dried using ambient air or air heated to a temperature no greater than about 100 degrees Celsius. WO2006/110407 describes pet food with two physically distinct components: a first component comprising a source of protein, a source of fat, and a source of carbohydrate, which may be at least partially extruded and a second, physically distinct component which comprises viable probiotic microorganisms. By keeping the matrix component and the micro-organisms separate, these applications thus inherently have more process steps, making the methods more complicated and expensive. Moreover, these processes are only applicable when the micro-organisms may be separated from the material (e.g. on the outside of the material) and cannot be used when the activity should be contained in, rather than on, the material.

The incorporation of unicellular or multicellular organisms in hydrophobic polymers has been suggested in WO2006/024115, for temperatures higher than 100° C., but still under standard pressure conditions. As this application however contains no examples with (unicellular or multicellular) organisms, it is unclear whether such organisms would still be viable when used in the preparation of the hydrophobic polymers described. This is not likely, however, since under these conditions, the water in the cells will start to boil.

To summarize, it is known in the art that material processing (e.g. polymer processing, food processing) is often conducted at high temperatures at which cells or organisms are not viable. Moreover, material processing often involves working at high pressure, especially if a material needs to be moulded, pelleted or extruded (e.g. also polymer processing, food processing). The pressure applied is also too high to ensure the viability of (micro-)organisms. Moreover in order for the organisms to be viable a minimal amount of water should be present in the processed materials. Indeed, if viability is reported at all, this is usually significantly decreased.

Thus, it would be beneficial to have methods available that allow the incorporation of viable micro-organisms in different materials, wherein the micro-organisms remain viable during high-pressure and/or high-temperature conditions applied during the production process of the material. This way, the produced materials may incorporate the beneficial properties of the micro-organisms.

SUMMARY OF THE INVENTION

Material processing temperatures are too harsh to allow incorporation of living or viable (micro-) organisms in materials such as natural or synthetic polymers, resins, foodstuffs, animal feed, and drugs. The same is true for pressures applied during material processing, e.g. in processes such as extrusion, pelletizing, pressure-cooking, thermo-molding, compression molding, injection molding, thermo-forming, impregnation, vacuum-forming, foaming, hot-melting or the like.

Surprisingly, it was found that specific bacteria (and particularly their spores) can be used that survive material processing temperatures without a significant loss in viability. Moreover, these bacteria can be incorporated in different materials at these temperatures and maintain their properties whilst incorporated in the material. Most notably, these specific bacteria withstand temperatures that are considerably higher than the ones usually envisaged when working with micro-organisms. Such high temperatures are however typical in the field of material processing (e.g. polymer processing, food processing, . . . ) and are typically in the range of 100-350° C., more particularly in the range of 120-300° C. even more particularly in the range of 130-300° C., most particularly in the range of 150-300° C. According to specific embodiments, the high end of the temperature range is limited (e.g. to increase viability) to 220° C., 210° C., 200° C. or even more particularly to between 150 and 200° C.

Further, specific bacteria (and particularly their spores) can be used that survive pressures applied during material processing without a significant loss in viability. Here also, these bacteria can be incorporated in different materials at these pressures and maintain their properties whilst incorporated in the material.

Thus, according to a first aspect, the invention relates to the identification and isolation of a micro-organism, in particular a spore-forming organism, able to withstand high temperatures while remaining viable. According to a second aspect, the invention relates to the identification and isolation of a micro-organism, in particular a spore-forming organism, able to withstand high pressures while remaining viable. According to particular embodiments, the organism (or its spores) is able to withstand both high temperatures and high pressures (either subsequently or concomitantly) while remaining viable.

According to particular embodiments, the present invention relates to A *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1).

According to another aspect, methods are provided herein for producing a material with viable organisms contained therein, comprising mixing
- a matrix selected from a natural or synthetic polymer, a resin, a foodstuff, an animal feed, and a drug; and
- living or viable spores of micro-organisms, which spores are viable at temperatures of between 100° C. and 350° C. and/or at a pressure of between 1.5 and 400 bar at a temperature of between 100° C. and 350° C. and/or at a pressure of between 1.5 and 400 bar.

According to particular embodiments, the micro-organisms or spores thereof are viable at temperatures of between 100° C. and 350° C. and at a pressure of between 1.5 and 400 bar.

According to particular embodiments, the mixing of the spores will be in dry conditions. According to very particular embodiments, dry conditions mean that less than 5000 ppm water are present, e.g. hygroscopic polymers can be dried to <5000 ppm water before being used. This particularly applies for non-food or non-feed matrices, as food or feed often will contain water. In alternative particular embodiments, mixing of the spores can be in wet conditions, but care will be taken to adapt pressure and temperature so that the boiling point of water is not reached in—or outside of the cells. Standard graphs are available in the art for the relation between the water boiling point and barometric pressure.

In further particular embodiments, the micro-organisms or spores thereof used in the methods are of the *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1).

In some embodiments, natural or synthetic polymers are used as matrix material in the methods of the application. According to particular embodiments, the polymer comprises at least one monomer selected from the group consisting of acrylates, methacrylates, acrylamides, methacrylamides, alcohols, amines, anhydrides, epoxides, styrenes, functionalized vinyls, functionalized allyls, propenes, butadienes, ethylenes, isocyanates, lactams, lactones, saccharides, glucose and esters.

According to further particular embodiments, the polymer is a polar polymer. Polarity values can be obtained from the art, e.g. from "The polymer handbook" (John Wiley and Sons), and are typically expressed in the Hildebrand parameter. These values typically range from between 12 (apolar) and 44 (extremely polar) $(MPa)^{1/2}$. For purposes of the present invention, a polymer can be called polar when it has a polarity value of at least 17, more particular at least 18, even more particular at least 19, yet even more particular at least 20, most particular at least 21 $(MPa)^{1/2}$.

According to alternative particular embodiments, the polymer has a minimal water absorption value. These values are measured as follows: the granulate-form polymers are first pressed into plates and dried at 70° C. The—beforehand—dried polymer plate is weighed, this results in mass M1. Afterwards, the plate is submersed in distilled water for a predetermined time and weighed again, after removal of the surface water. This results in mass M2. In function of time, the water absorption value is determined with the following formula:

$$\text{wt \%} = (M2-M1)*100/M1$$

Every measurement is preferably done twice and the average should be taken. According to particular embodiments, the water absorption should be at least 0.01, particularly at least 0.02, more particularly at least 0.1, most particularly at least 0.2.

According to more specific embodiments, the polarity and water absorption value are combined, e.g. the polymer has a polarity value of at least 17 $(MPa)^{1/2}$ and a water absorption value of at least 0.01, depending on the desired properties. Increased water absorption indicates the polymer will absorb more water over time, increased polarity values are indicative of bigger interaction forces between the polymer chains and a polar solvent, i.e. water. The polarity of a polymer depends on the solubility in a given solvent, which in turn depends on the chemical structure, amount of chain branching and crystallinity.

According to a very particular embodiment, the polymer is $O_2$-permeable.

According to specific embodiments, the (matrix) material, and thus also the resulting product, is for human or animal consumption and the micro-organisms or spores thereof are a probiotic.

In specific embodiments of the methods disclosed herein, an additional step is performed, which can be selected from an extrusion step, a pelletizing step, a pressure-cooking step, a thermo-molding step, a compression molding step, an injection molding step, a thermo-forming step, an impregnation step, a vacuum-forming step, a foaming step or a hot-melt step. This step can be performed during or after the mixing.

According to further particular embodiments, the extrusion step, pelletizing step, pressure-cooking step, thermo-molding step, compression molding step, injection molding step, thermo-forming step, impregnation step, vacuum-forming step, foaming step or hot-melt step is performed at a temperature of between 100° C. and 350° C. and/or at a pressure of between 1.5 and 400 bar. It is to be understood that temperature and pressure used in the methods will be adapted as much as possible to ensure maximal viability of the micro-organisms while still being able to manipulate the matrix material as desired.

According to a further aspect the present invention relates to a material with viable micro-organisms or spores thereof contained therein, said material comprising a matrix selected from a natural or synthetic polymer, a resin, a foodstuff, an animal feed and a drug as well as the use of said material. In a more specific embodiment the viable micro-organism is a *Bacillus amyloliquefaciens strain* deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1). In another specific embodiment the matrix is a polar polymer.

According to another aspect the present invention relates to the use of living or viable spores of micro-organisms, which spores are viable at temperatures between 100° C. and 350° C. and/or at a pressure of between 1.5 and 400 bar, for the production of materials with viable micro-organisms contained therein. In a more specific embodiment the living or viable spores are derived from *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1).

DETAILED DESCRIPTION

Definitions

Figure 1:
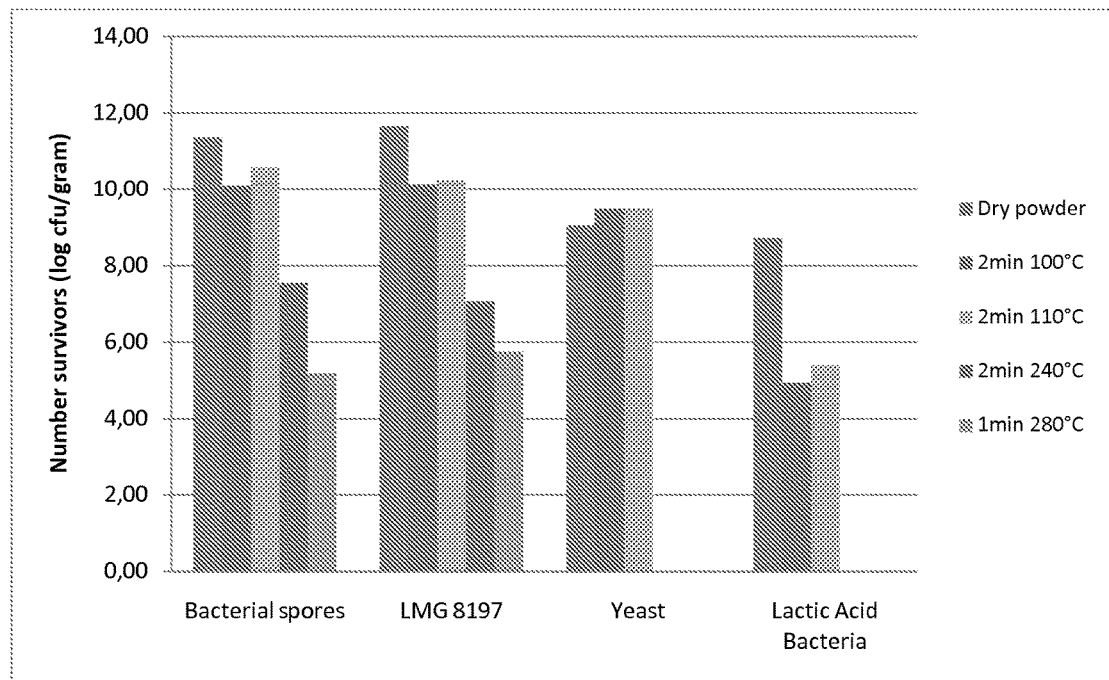
FIG. 1 shows the dry heat resistance of different micro-organisms. 1: Strain ID9698 (identified as *Bacillus amyloliquefaciens*); 2: LMG 8197: *Bacillus subtilis* subsp. *Spizizenii;* a *bacterium* of which the gyrA sequence shows >70% sequence identity to SEQ ID NO:1; 3: Enterol®: Commercially available drug with living yeasts (probiotic) (*Saccharomyces boulardii*); 4: Probactiol®: Commercially available drug with living lactic acid bacteria (probiotic) (1/1 mix *Lactobacillus acidophilus* NCFM en *Bifidobacterium lactis* BI-07). From left to right, the columns represent different heat treatments.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

A "spore" or "endospore" as used herein is a dormant, tough, and non-reproductive structure produced by a number of bacteria. The primary function of spores is to ensure the survival of a *bacterium* through periods of environmental stress. They are therefore resistant to ultraviolet and gamma radiation, desiccation, lysozyme, temperature, starvation, and chemical disinfectants. Spores are commonly found in soil and water, where they may survive for long periods of time. Some bacteria produce exposures or cysts instead, but cysts differ from (endo)spores in the way they are formed and also the degree of resistance to unfavorable conditions. Spores are much more resistant than cysts.

A "polar polymer" as used in the application refers to polymers that are classified as polar using solubility parameters. Solubility parameters are well known in the art and include e.g. the Hansen parameters and Hildebrand parameters. Hildebrand parameters are expressed in the unit $(MJ/m^3)^{1/2}$ or $MPa^{1/2}$. The Hildebrand solubility parameter (δ)

provides a numerical estimate of the degree of interaction between materials, and can be a good indication of solubility, particularly for non polar materials such as many polymers. Materials with similar values of δ are likely to be miscible. The higher the Hildebrand parameter, the more polar the polymer. For the purposes of the present invention, a polar polymer is defined as having a Hildebrand parameter of 17 or higher, 18 or higher, 19 or higher or more particularly 20 or most particular at least 21 $(MPa)^{1/2}$ or higher.

A "probiotic" as used in the present application refers to live microorganisms which when administered in adequate amounts confer a health benefit on the host.

According to a first aspect, the invention relates to the identification and isolation of a micro-organism, in particular a spore-forming organism, able to withstand high temperatures while remaining viable. High temperatures are typically within the range of 100° C. to 350° C., more particularly within the range of 120° C. to 350° C., 130° C. to 350° C., 140° C. to 350° C., 150° C. to 350° C., 120° C. to 300° C., 130° C. to 300° C., 140° C. to 300° C., 150° C. to 300° C. Alternatively, high temperatures can be defined as temperatures above 100° C., 110° C., 120° C. or 130° C. but not over 220° C., 210° C., 200° C., 190° C., 180° C., 170° C., 160° C., or 150° C. According to particular embodiments, the micro-organisms (or their spores) remain viable when subjected to these temperatures for a prolonged period of time. Typical time periods these micro-organisms (spores) can survive temperatures in the above ranges include up to 30 seconds, up to 45 seconds, up to 1 minute, up to 90 seconds, up to 2 minutes, up to 150 seconds, up to 3 minutes, up to 210 seconds, up to 4 minutes, up to 270 seconds, up to 5 minutes, up to 6 minutes, up to 7 minutes, up to 8 minutes, up to 9 minutes, up to 10 minutes, up to 15 minutes, up to 20 minutes, up to 25 minutes, up to 30 minutes, up to 45 minutes, up to 1 hour, up to 2 hours, up to 3 hours, up to 4 hours, up to 5 hours, up to 6 hours, up to 12 hours, up to 24 hours, up to 48 hours, up to 72 hours or even longer.

According to a second aspect, the invention relates to the identification and isolation of a micro-organism, in particular a spore-forming organism, able to withstand high pressures while remaining viable. High pressures are typically within the range of 1.5 to 400 bar, 2 to 400 bar, 3 to 400 bar, 4 to 400 bar, 5 to 400 bar, 10 to 400 bar, 20 to 400 bar, 25 to 400 bar, 30 to 400 bar, 40 to 400 bar, 50 to 400 bar, 75 to 400 bar, 100 to 400 bar, 150 to 400 bar, 200 to 400 bar, 250 to 400 bar, 300 to 400 bar, 1.5 to 350 bar, 2 to 350 bar, 3 to 350 bar, 4 to 350 bar, 5 to 350 bar, 10 to350 bar, 20 to 350 bar, 25 to 350 bar, 30 to 350 bar, 40 to 350 bar, 50 to 350 bar, 75 to 350 bar, 100 to 350 bar, 150 to 350 bar, 200 to 350 bar, 250 to 350 bar, 300 to 350 bar. Sometimes the upper limit can be lower, e.g. pressures up to 250 bar, up to 200 bar, up to 150 bar, up to 100 bar, up to 50 bar, up to 40 bar, up to 30 bar, up to 25 bar, up to 20 bar, up to 10 bar, up to 5 bar. A bar equals 100 kPa and 0.98692 atmosphere.

According to particular embodiments, the above-mentioned micro-organism is of a *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence (SEQ ID NO:1) of the *Bacillus amyloliquefaciens* strain deposited under No. ID9698 at the BCCM. According to further particular embodiments, the gyrA sequence is at least 75% identical, at least 80% identical, at least 85% identical, at least 87% identical, at least 90% identical, at least 91% identical, at least 92% identical, at least 93% identical, at least 94% identical, at least 95% identical, at least 96% identical, at least 97% identical, at least 98% identical or even at least 99% identical to SEQ ID NO:1.

Percentage sequence identity is calculated according to methods known in the art, e.g. the BLAST algorithm. The following terms are typically used to describe the sequence relationships between two or more nucleic acids or polynucleotides: (a) "reference sequence", (b) "comparison window", and (c) "percentage of sequence identity".

(a) As used herein, "reference sequence" is a defined sequence used as a basis for sequence comparison. A reference sequence may be a subset or the entirety of a specified sequence; for example, a segment of a full-length gyrA sequence (such as e.g. SEQ ID NO:1), or the complete gyrA sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length and optionally can be 30, 40, 50, 100 or more contiguous nucleotides in length. Those of skill in the art understand that to avoid a high similarity to a reference sequence due to inclusion of gaps in the polynucleotide sequence, a gap penalty is typically introduced and is subtracted from the number of matches. Note that to align sequences dissimilar in length, the comparison window will usually be determined using the shorter of the two sequences.

(c) As used herein, "percentage of sequence identity" means the value determined by comparing two optimally aligned sequences over a comparison window, wherein the portion of the polynucleotide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Methods of aligning sequences for comparison are well known in the art. Gene comparisons can be determined by conducting BLAST (Basic Local Alignment Search Tool; Altschul, S. F., et al., (1993) J. Mol. Biol. 215:403-410; see also, www.ncbi.nlm.nih.gov/BLAST/) searches under default parameters for identity to sequences contained in the BLAST "GENEMBL" database. A sequence can be analyzed for identity to all publicly available DNA sequences contained in the GENEMBL database using the BLASTN algorithm under the default parameters.

The ID9698 strain is characterized by a particular high resistance to elevated temperatures, even in the ranges cited above. According to a particular embodiment, the elevated temperatures are during a dry heat treatment. These ranges are also within the typical range of temperatures applied during material processing, in particular during natural polymer processing, synthetic polymer processing, resin processing, food or feed processing, or the processing of pharmaceutical compositions (drugs). The spores of the micro-organism retain their viability, even if subjected to these temperatures for the different time periods typically applied during material processing (which may range from about 15 seconds up to the time ranges mentioned above).

Also characteristic of the ID9698 strain is the particularly high resistance to elevated pressures, even in the ranges cited above. These ranges are also within the typical range of pressures applied during material processing, in particular during natural polymer processing, synthetic polymer processing, resin processing, food or feed processing, or the processing of pharmaceutical compositions (drugs), e.g. during steps like extrusion, pelletizing, pressure-cooking, thermo-molding, compression molding, injection molding, thermo-forming, impregnation, vacuum-forming, foaming, hot-melting or the like. The spores of the micro-organism retain their viability, even if subjected to these pressures for the different time periods typically applied during material processing (which may range from about 15 seconds up to the time ranges mentioned above).

Material processing may involve a high-temperature step, a high-pressure step, or both. If both a high-temperature step and high-pressure step are present in the material processing method, these can occur concomitantly (the material is subjected to high pressure and high temperature at the same time) or subsequently (a high temperature step is followed (although not necessarily immediately) by a high pressure step, or vice versa). Examples of material processing involving both high-pressure and high-temperature steps include pelletizing (e.g. between 70° C. and 90° C. under 1.5 bar) and extrusion (e.g. between 125° C. and 150° C. under 30 to 40 bar; for food or feed products, the dough will typically contain 200-300 g moisture/kg).

According to a further aspect, methods are provided for using the thermo-resistant and/or pressure-resistant micro-organism, as described above, in the production of materials. The obtained materials incorporate at least one new property, which is the direct result of the incorporation of the micro-organism.

Accordingly, methods are provided for producing a material with viable organisms contained therein, comprising mixing
 a matrix selected from a natural or synthetic polymer, a resin, a foodstuff, an animal feed, and a drug; and
 living or viable spores of micro-organisms, which spores are viable at temperatures of between 100° C. and 350° C. and/or at a pressure of between 1.5 and 400 bar
at a temperature of between 100° C. and 350° C. and/or at a pressure of between 1.5 and 400 bar.

According to particular embodiments, the micro-organisms are distributed evenly (homogenously) throughout the matrix/processed material.

According to specific embodiments, the micro-organisms or spores thereof are viable at temperatures of between 100° C. and 350° C. as well as at a pressure of between 1.5 and 350 bar. According to further specific embodiments, the mixing of the matrix and the materials occurs only at elevated temperatures (i.e. between 100 and 350° C., more particularly between 100 and 220° C., more particularly between 110° C. and 200° C.). According to yet even more specific embodiments, the elevated temperatures are reached during dry heat treatment. According to alternative specific embodiments, the mixing of the matrix and the materials occurs only at elevated pressures (i.e. between 1.5 and 400 bar). According to further alternative specific embodiments, the mixing of the matrix and the materials occurs both at elevated temperatures and pressures.

Note that the period of time the elevated temperature and/or elevated pressure is maintained will depend on the particular process, and may be significantly different, typically depending on the material of the matrix (which e.g. has its particular melting point, and plasticity characteristics). However, a person skilled in the art can apply known processes depending on the material he works with, and will be able to use the temperatures and pressures described for such processes, as well as the amount of time such temperature or pressure should be applied. Typically, the temperature or pressure will be elevated (between 100 and 350° C. or between 1.5 and 400 bar) for at least 2 seconds, at least 5 seconds, at least 10 seconds, at least 20 seconds, at least 30 seconds, at least 40 seconds, at least 50 seconds, at least one minute, at least 70 seconds, at least 80 seconds, at least 90 seconds, at least 100 seconds, at least 110 seconds, at least 2 minutes, at least 5 minutes, at least 10 minutes. Maximal lengths of time will also depend on the process, but will typically be up to 30 seconds, up to 45 seconds, up to 1 minute, up to 90 seconds, up to 2 minutes, up to 150 seconds, up to 3 minutes, up to 210 seconds, up to 4 minutes, up to 270 seconds, up to 5 minutes, up to 6 minutes, up to 7 minutes, up to 8 minutes, up to 9 minutes, up to 10 minutes, up to 15 minutes, up to 20 minutes, up to 25 minutes, up to 30 minutes, up to 45 minutes, up to 1 hour, up to 2 hours, up to 3 hours, up to 4 hours, up to 5 hours, up to 6 hours, up to 12 hours, up to 24 hours, up to 48 hours, or up to 72 hours.

Some organisms are particularly suitable for being viably incorporated in the matrix in the methods described herein. Accordingly, in particular embodiments it is envisaged that the micro-organisms or spores thereof are of the *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1).

During the production process of an industrial product, such as packaging material, textile fibers, granules or the like, the micro-organisms (and in particular the spores thereof) and the material (e.g. polymer, food or feed product, pharmaceutical composition) are mixed together within a—usually short—period of time during which the matrix material is liquid, thus at a temperature above its melting point or processing temperature. According to a particular embodiment, the liquid material is not boiling and temperature and pressure conditions are chosen such that the boiling point of water is not reached.

The incorporated micro-organisms typically remain inactive as long as the conditions (e.g. temperature, pressure, drought) are unfavorable. However, as soon as the living conditions become favorable, the spores change into active, metabolizing cells, with beneficial properties. The favorable ambient conditions usually precede or coincide with the product starting to be used in association with an environment which is suitable for life in terms of temperature, pressure and relative humidity. As long as conditions are favorable, the biologically active form will perform its intended function. If conditions return to stress conditions, the active form of the micro-organism will revert to the spore form.

During processing, the inactive forms of the bacteria are encapsulated in a continuous phase, defined as the matrix. Preferably, the encapsulation results in a homogeneous distribution of the organisms. These organisms can have multiple functions, a number of possible applications is presented hereunder.

According to particular embodiments, the matrix material used is a natural or synthetic polymer. Natural polymers include for instance cellulose and other polysaccharides. A wide variety of synthetic polymers exists, and many of them are very important industrial compounds (e.g. PET, PVC, PE, PU, PLA, PP, . . . ). According to specific embodiments, the natural or synthetic polymer comprises at least one monomer selected from the group consisting of acrylates, methacrylates, acrylamides, methacrylamides, alcohols, amines, anhydrides, epoxides, styrenes, functionalized vinyls, functionalized allyls, propenes, butadienes, ethylenes, isocyanates, lactams, lactones, saccharides, glucose and esters.

The property or organism incorporated will typically vary depending on the type of use envisaged afterwards. A particularly significant application area is in the food packaging sector which employs what is known as an oxygen barrier, e.g. in multi-layer packaging material for foodstuffs, such as PET bottles. Such bottles can be used for beverages, such as beers or fruit juices. The matrix material in this case is the polymer PET, while micro-organisms able to withstand the high temperatures of the production process are used. When the package is being filled with beverages, for example, the internal environment of the PET becomes water-saturated, with the result that the (spores of the) micro-organisms are activated to form respiring cells which consume all the oxygen present inside the bottle. This is beneficial to prevent oxidation of the content of the package (e.g. food or drinks). Also, all the external oxygen which can diffuse through the wall is captured by the micro-organisms for respiration, which results in an efficient oxygen barrier.

In another embodiment, a carbon dioxide barrier is provided in the case the micro-organisms consume carbon dioxide, or alternatively produce carbon dioxide that desorbs in the content or acts as an osmotic barrier.

Note that these applications require that the dehydrated/desiccated organisms can be rehydrated. Thus, the polymer used for such applications should be able to become water-saturated, i.e. the polymer must be able to become sufficiently hydrated so that the spores therein can increase their water content and revert to metabolically active organisms. This may be achieved by using a polar polymer. According to particular embodiments, the polymer used as matrix component is a polar polymer. Alternatively or additionally, a polymer having a sufficiently high water absorption value is used. According to particular embodiments, the $H_2O$ absorption value of the polymer is at least 0.01; at least 0.02; at least 0.1 or at least 0,2. According to very specific embodiments, the polymer is a polar polymer with a sufficiently high water absorption value.

A further example of a use consists in the action as a UV blocker, which works in a similar way to the above example. For such cases, micro-organisms should be used of which the spores very intensively block UV light (typically, such spores contain a high concentration of astaxanthin). This feature can be used in moisture-resistant UV-proof films and polymer coverings.

Another example of the use of the present methods is in the preparation of materials for human or animal consumption, e.g. foodstuffs, animal feed or kibble, drugs, pharmaceutical preparations and the like. Typically, the micro-organism to be incorporated therein will be used for its beneficial properties on the health of the organism when ingested, i.e. it is a probiotic. Probiotic bacterial or yeast cultures are intended to assist the body's naturally occurring gut flora, an ecology of microbes, to re-establish themselves. They are sometimes recommended after a course of antibiotics, or as part of the treatment for gut related candidiasis. Claims are made that probiotics strengthen the immune system to combat allergies, excessive alcohol intake, stress, exposure to toxic substances, and other diseases. In these cases, the bacteria that work well with our bodies may decrease in number, an event which allows harmful competitors to thrive, to the detriment of our health. Probiotics have been shown to be beneficial in e.g. managing lactose intolerance, prevention of colon cancer, cholesterol lowering, lowering blood pressure, improving immune function, preventing infections, treatment of *Helicobacter pylori* infections, reduction of antibiotic-associated diarrhea, reducing inflammation, improving mineral absorption, prevention of harmful bacterial growth under stress, and improving symptoms of irritable bowel syndrome and ulcerative colitis.

According to particular embodiments, the (matrix) material is for human or animal consumption and the micro-organisms or spores thereof are a probiotic.

Micro-organisms or their spores can for instance be incorporated as a powder, or as a lyophilized powder, as is known to the person of skill in the art. Other forms may be envisaged as well, depending on the type of matrix material or the process performed.

During material processing, it will often happen that the material needs to be in a certain shape. Food, feed and drugs for instance are often extruded, animal feed is often pelleted, polymers may be moulded in a particular shape. These processes are known to a person skilled in the art. Whereas now this is typically done prior to the adding of micro-organisms (Biourge et al., 1998), the methods presented herein allow the adding of micro-organisms before such processing step, while the organisms remain viable. This is not only simpler and more cost-effective, but also has the added benefit that the micro-organisms can be incorporated evenly throughout the material.

Accordingly, methods are provided wherein an extrusion step, a pelletizing step, a pressure-cooking step, a thermo-molding step, a compression molding step, an injection molding step, a thermo-forming step, an impregnation step, a vacuum-forming step, a foaming step or a hot-melt step is performed during or after the mixing of the matrix material and the micro-organisms or spores thereof.

According to further specific embodiments, the extrusion step, pelletizing step, pressure-cooking step, thermo-molding step, compression molding step, injection molding step, thermo-forming step, impregnation step, vacuum-forming step, foaming step or hot-melt step is performed at a temperature of between 100° C. and 350° C. According to alternative specific embodiments, the extrusion step, pelletizing step, pressure-cooking step, thermo-molding step, compression molding step, injection molding step, thermo-forming step, impregnation step, vacuum-forming step, foaming step or hot-melt step is performed at a pressure of between 1.5 and 400 bar. According to yet further alternative embodiments, the extrusion step, pelletizing step, pressure-cooking step, thermo-molding step, compression molding step, injection molding step, thermo-forming step, impregnation step, vacuum-forming step, foaming step or hot-melt step is performed at a temperature of between 100° C. and 350° C. and at a pressure of between 1.5 and 400 bar. (Note that it is possible that the material is subjected to increased temperature subsequent to increased pressure or vice versa, the fact that both occur during this processing step does not automatically imply that temperature and pressure are increased at the same time, although this is also a possibility).

According to a further aspect the present invention relates to a material with viable micro-organisms or spores thereof contained therein, said material comprising a matrix selected from a natural or synthetic polymer, a resin, a foodstuff, an animal feed and a drug. More particularly the material is obtained by the method of the invention as described above.

In a specific embodiment the viable micro-organisms in the material are thermo-resistant and/or pressure resistant organisms as described above. Even more specific the viable micro-organism is a *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1). In an additional embodiment the matrix of the material described above is a polar polymer.

According to a specific embodiment the material is a polar polymer as described above containing viable thermo-resistant and/or pressure resistant micro-organisms such as, but not limited to a *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1).

According to an alternative embodiment the present invention relates to the use of a polar polymer containing viable aerobic thermo-resistant and/or pressure resistant micro-organisms therein as an oxygen barrier.

According to another aspect the present invention relates to the use of living or viable spores of micro-organisms, which spores are viable at temperatures between 100° C. and 350° C. and/or at a pressure of between 1.5 and 400 bar, more particularly viable at temperatures between 100° C. and 220° C. and/or at a pressure of between 1.5 and 50 bar, for the production of materials with viable organisms therein. In a more specific embodiment the living or viable spores are derived from *Bacillus amyloliquefaciens* strain deposited under No. ID9698 at the Belgian Co-ordinated Collections of Micro-organisms (BCCM), or a *Bacillus* strain of which the gyrA sequence is at least 70% identical to the partial gyrA sequence of the *Bacillus amyloliquefaciens* strain deposited under No. ID9698 at the BCCM (SEQ ID NO:1).

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

Characterisation of *Bacillus amyloliquefaciens*

Culture of Micro-Organisms

Four different colony types (ID9698 t1, ID9698 t2, ID9698 t3 and ID9698 t4) could be isolated from the original material, which were purified and analyzed individually. The original material was obtained from Biougra in Morocco, an arid area of the Anti-Atlas, where a chance existed to find spores that are resistant to extreme high temperatures in the summer on dry organic substrate that is exposed to solar radiation.

A fatty acid analysis was performed and all four cultures were allocated to the group of '*Bacillus* and related taxa'. Subsequently, a partial 16S rDNA sequence analysis was performed and all four cultures were identified as belonging to the *Bacillus subtilis*-complex.

Further Identification of ID9698 t1 Using Partial gyrA Sequence Analysis.

Partial gyrA sequence analysis and phylogenetic study: the applicability of the gyrA sequence for species discrimination within the *Bacillus subtilis* complex has been reported by Chun and Bae (Chun J. and Bae K. S. 2000. Phylogenetic analysis of *Bacillus subtilis* and related taxa based on partial gyrA gene sequences. Antonie van Leeuwenhoek 78: 123-127) and has already been successfully demonstrated. The gyrA gene was amplified by PCR, starting from the DNA extracted in the frame of the RAPD analysis. PCR amplified gyrA was purified using the NucleoFast® 96 PCR Clean-up Kit (Macherey-Nagel, Düren, Germany).

Sequencing reactions were performed using the BigDye® Terminator Cycle Sequencing Kit (Applied Biosystems, Foster City, Calif., USA) and purified using the BigDye® XTerminatorT Purification Kit (Applied Biosystems, Foster City, Calif., USA). Sequencing was performed using an ABI Prism® 3130XL Genetic Analyzer (Applied Biosystems, Foster City, Calif., USA). The primers were chosen with a partial overlap of sequences, ensuring highly reliable assembled data.

Sequence assembly was performed by using the program AutoAssembler™ (Applied Biosystems, Foster City, Calif., USA).

A similarity matrix was created using the software package BioNumerics (Applied Maths, Belgium) by homology calculation with a gap penalty of 0% and after discarding unknown bases and is based on pairwise alignment using an open gap penalty of 100% and a unit gap penalty of 0%. Phylogenetic analysis was performed using the software package BioNumerics (Applied Maths, Belgium) after including the consensus sequence in an alignment of small ribosomal subunit sequences collected from the international nucleotide sequence library EMBL. A resulting tree was constructed using the neighbor-joining method.

Conclusions

1. The phylogenetic position of ID9698 t1 is clearly in the *Bacillus subtilis*-complex.

2. The high gyrA sequence similarities (95.9-99.7%) found with several *Bacillus amyloliquefaciens* strains demonstrate that ID9698 t1 belongs to this species.

Example 2

Dry Heat Resistance of Micro-Organisms

Material and Methods

Micro-Organisms Tested

1. Strain ID9698 (identified as *Bacillus amyloliquefaciens*)

2. LMG 8197: *Bacillus subtilis* subsp. *Spizizenii*; a bacterium of which the gyrA sequence shows >70% sequence identity to SEQ ID NO:1.

3. Enterol®: Commercially available drug with living yeasts (probiotic) (*Saccharomyces boulardii*)

4. Probactiol®: Commercially available drug with living lactic acid bacteria (probiotic) (1/1 mix *Lactobacillus acidophilus* NCFM en *Bifidobacterium lactis* BI-07)

The same numbering was used in the results.

Dry Heat Treatment

A known quantity of powder of the different micro-organisms was transferred to a glass test tube of 8 mm diameter (VWR, article 212-0011) and closed with the appropriate plastic lid. The test tubes were maximally ¼ full. The test tubes were ¾ submerged in frying oil of 100° C.±0.1 and 110° C.±0.1 and in a metal bath of 240° C.±5 and 280° C.±5 (only for *Bacillus*). The temperature of the bath was followed with a thermocouple with data logger.

In all treatments, the temperature was also followed in a ¼-sand filled test tube. From these measurements it appeared that it took 1 minute to warm the sample to the desired temperature. This temperature was maintained for 1 additional minute (2 minutes of treatment). Only the yeast sample was submerged for only 1 minute at 240° C., because 2 minutes was not physically feasible (excessive foaming of the sample). Also, the *Bacillus* samples were only treated 1 minute at 280° C.

After treatment, 1 ml of PPS was added to the test tubes and a dilution series was spread on plates. All plates were counted after an incubation of 48 h at 30° C. An extra day of incubation at 30° C. did not result in extra colonies. For all *Bacillus* strains, incubation was on "Fortified Nutrient Agar" (NA+), for lactic acid bacteria on "Man, Rogosa and Sharp agar" (MRS) and for yeast on "Yeast Extract Glucose Chloramphenicol Agar" (YGC).

All measurements were performed in duplicate and the results were expressed in log cfu/gram powder.

Results

From the results, shown in FIG. 1, it appeared that the lactic acid bacteria at 100° C. en 110° C. already showed a reduction of ±3.50 log. At these temperatures, the reduction for *Bacillus* strains was ±1-1.5 log units, while for the yeast strain no reduction was observed (although colony forming potential was initially already lower there).

At 240° C., both the yeast and lactic acid bacteria still show a small growth. This was however very small: in both samples, the number cfu decreased in absolute values from >10$^8$ cfu to 10 cfu. This small percentage of survivors can completely be attributed to micro-organisms on the lid of the test tube. This part of the sample was not submerged, and thus not heated in the same degree.

In a second experiment with a slightly different setup, the dry heat resistance of the *Bacillus amyloliquefaciens* strain ID9698 was compared with that of yeast and lactic acid bacteria.

Material and Methods

Micro-Organisms Tested

1. Strain ID9698 (identified as *Bacillus amyloliquefaciens*)
2. Yeast: Bakery yeast Bruggeman instant (Algist Bruggeman, Ghent) (*Saccharomyces cerevisiae*)
3. Probactiol®: Commercially available drug with living lactic acid bacteria (probiotic) (1/1 mix *Lactobacillus acidophilus* NCFM en *Bifidobacterium lactis* BI-07)

Dry Heat Treatment

Dry heat treatments were conducted in a Thermogravimetric Analyzer (TGA). The treatment temperature varied from 100° C. to 240° C. with a 10° C. interval.

A known aliquot (about 15 mg) of dry powder containing 10.89 log spores/g *B. amyloliquefaciens*, 10.17 log cfu/g yeast or 9.09 log cfu/g lactic acid bacteria respectively was placed in a, to the treatment temperature, preheated TGA and heat treated for 2 min.

The powder was transferred to a sterile eppendorf and resuspended in 1 ml of sterile physiological solution (PPS). Afterwards, appropriate dilutions were plated on Fortified Nutrient Agar for *B. amyloliquefaciens,* on "de Man, Rogosa and Sharp agar" (MRS) for lactic acid bacteria and on "Yeast Extract Glucose Chloramphenicol Agar" (YGC) for yeast. All plates were incubated for 3 days at 30° C. before counting.

Results

The results showed a severe difference in heat stability of the tested micro-organisms. At a treatment temperature of 130° C., more than 5 log reduction occurred for the lactic acid bacteria (see Table 1). At the same temperature, almost no reduction was observed for *B. amyloliquefaciens* and yeast.

For yeast, severe reduction occurred at a treatment temperature of 150° C. (3.61 log), whilst for *B. amyloliquefaciens* almost no reduction (<1 log) was found until 180° C.

TABLE 1

Reduction (log cfu) in 15 mg sample of dry powder

| Heat treatment (° C.) | Micro-organisms | | |
|---|---|---|---|
| | Strain ID9698 | Lactic acid | Yeast |
| Room temperature | 0.00 | 0.00 | 0.00 |
| 100 | 0.35 | 1.81 | 0.23 |
| 110 | 0.00 | 2.29 | 0.64 |
| 120 | 0.41 | 2.92 | 0.50 |
| 130 | 0.45 | 5.12 | 0.74 |
| 140 | 0.50 | >5.12 | 0.58 |
| 150 | 0.51 | | 3.61 |
| 160 | 1.19 | | >8.62 |
| 170 | 0.99 | | |
| 180 | 1.68 | | |
| 190 | 1.82 | | |
| 200 | 4.99 | | |
| 210 | 5.81 | | |
| 220 | >6 | | |

Results noted with ">" are under the detection limit

In a set of other, comparable experiments to evaluate dry heat resistance of yeast using smaller volumes, severe reduction of colony growth was already observed from 130° C. (data not shown).

Example 3

Analysis of Water Absorption of Polymers

Figure 2:
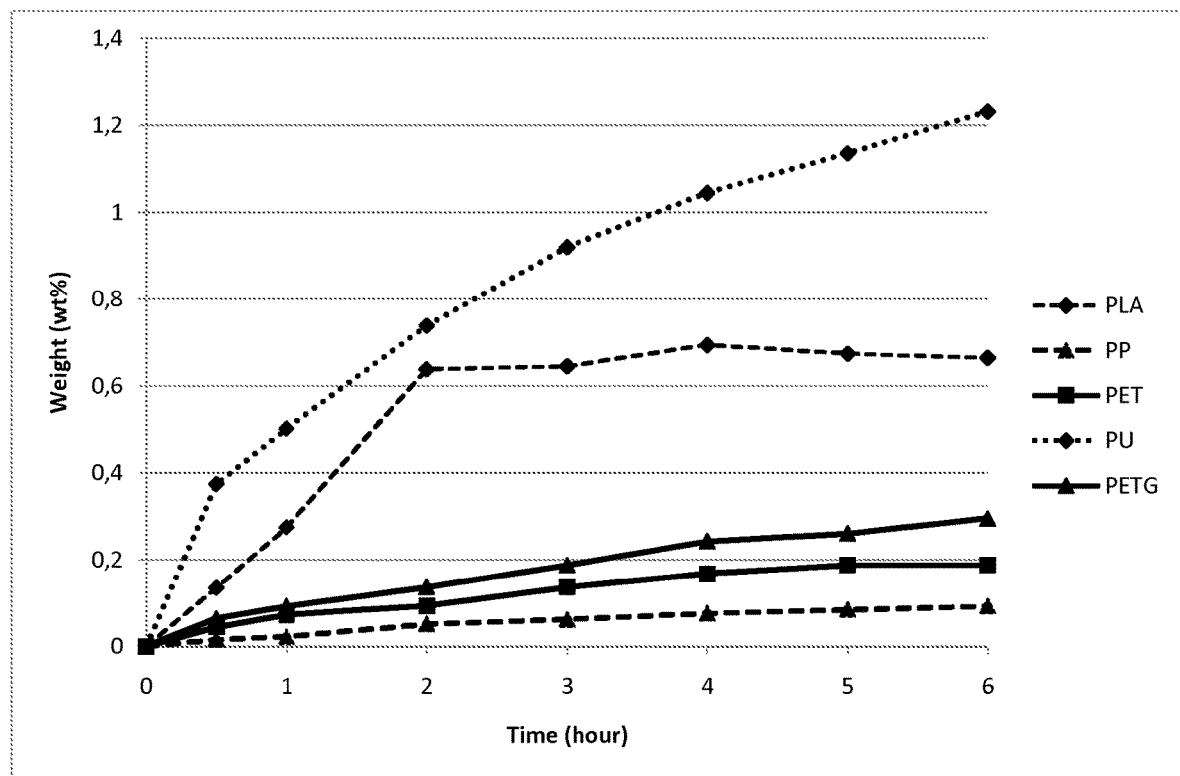
In FIG. 2, the water absorption of different polymers is shown in function of time: Prop (Poly Propylene or PP), PLA (Poly lactic acid), PETg (Poly Ethyleen Tereftalaat-1,4 cyclohexaandimethanol), PET (Poly Ethyleen Tereftalaat), PU (Poly Urethane).
Figure 3:
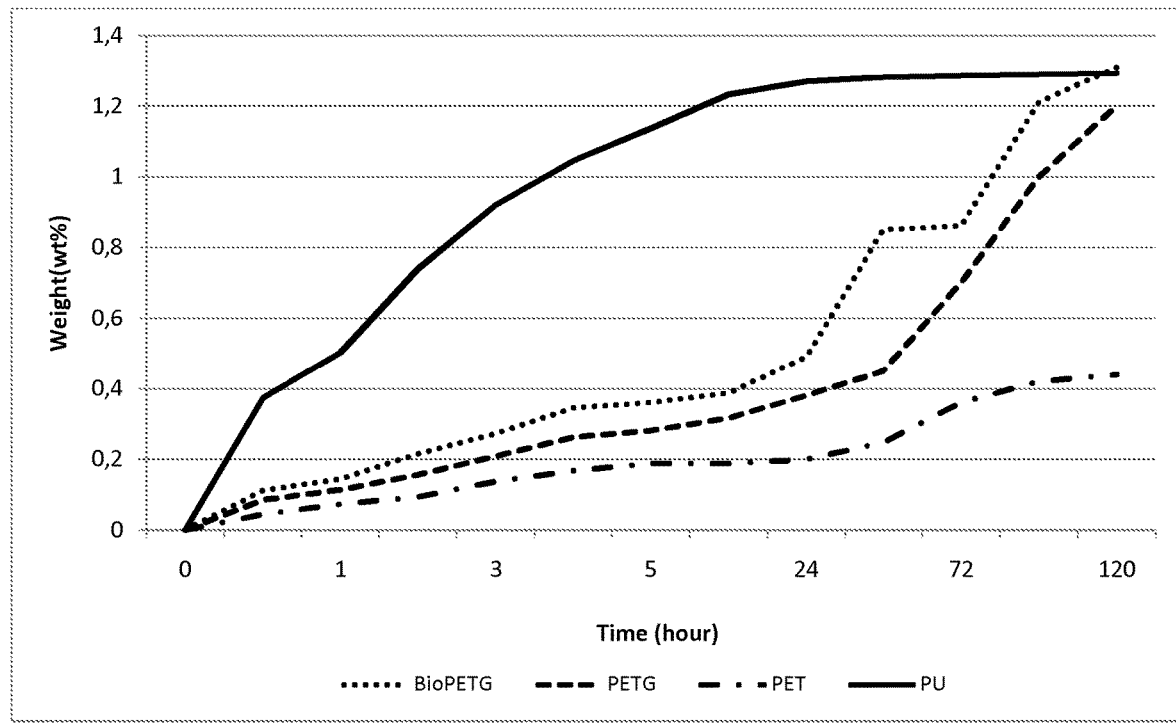
FIG. 3 also represents the water absorption of different polymers in function of time. The same abbreviations as in FIG. 2 are used. BioPETg is PETg with a mixture of *Bacillus amyloliquefaciens* spores incorporated therein according to the methods described herein.
Figure 4:
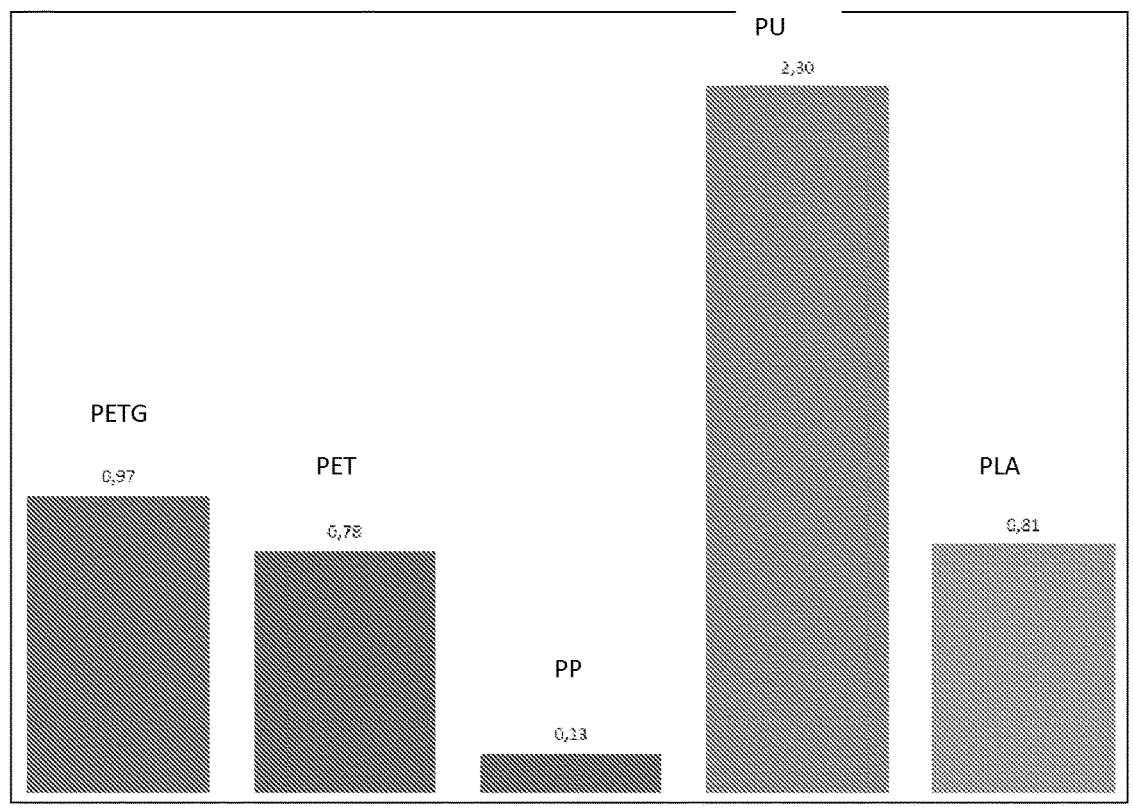
FIG. 4 shows the liquid content in percent after being exposed to 100% humidity for 3 days.

For all tested polymers, an increase in water absorption in function of time could be observed (FIGS. 2 and 3). In FIG. 3, PU shows an extremely high water absorption, this in contrast to the other three polymers. In these measurements, PU reaches a plateau after 3 days. For PETg en BioPETg (i.e. a mixture of *Bacillus amyloliquefaciens* spores with PETg), high absorption values are also observed. In FIG. 3, a small difference between the two polymers can clearly be observed. A plateau for BioPETg was obtained from day 1 to day 3. From day 4, an increase can be observed. A low water absorption for PET in function of time could be expected. FIG. 4 shows the liquid content in percent after being exposed to 100% humidity for 3 days.

Table 2 lists the Polarity values and water absorbance values for a few polymers.

TABLE 2

| Polymer | Polarity | H2O-absorbance |
|---|---|---|
| PETg | — | 0.296 |
| PET | 21.9 | 0.188 |
| PU | 22.9 | 1.232 |
| PLA | 21.0 | 0.670 |
| PP | 19.2 | 0.129 |
| PE | ±18 | 0.055 |
| HDPE | — | 0.022 |
| PC | — | 0.206 |

Example 4

Determination of the Surviving Spores After High Temperature and Pressure Incorporation in a Polyester Introduction Dry spore material was incorporated under high temperature and pressure in polyesters. The survival rate of spores after the incorporation process was determined by extracting the spores from the polyester. Living spores were quantified by plating out techniques.

Material and Methods

Dry spore powder was produced by a suitable fermentation process and downstream processing.

Dry spores were incorporated in polyester. As a typical example of a polyester, PETG was used. Incorporation was done with a polymer press in a 4% w/w concentration. Plates of the polymer without spores (blanc) were pressed for 5 min at 210° C., at a pressure of 10 kN. Dry spore powder was pressed in the correct concentration between two blanc polymer plates, to obtain one new sample with the spores incorporated. Processing was done for 5 min at 210° C. and 29 bar.

0.02 g of the polymer plate with incorporated spores was dissolved in a 1/1 chloroform ($CHCl_3$)/demineralised water mixture. This was done in an ultrasonic bath for 10 min. During the dissolution process, spores are released from the polymer into the chloroform fraction. Due to intensive stirring, the released spores immediately migrate to the water fraction.

After dissolution, phase separation between the polymer containing chloroform fraction and the spore containing water fraction occurred. The amount of living spores in the water fraction was determined by making the appropriate decimal dilutions in PPS and spread plating on nutrient agar (NA). NA plates were incubated for 48 h at 30° C. before counting.

Results and Conclusion

Figure 5:
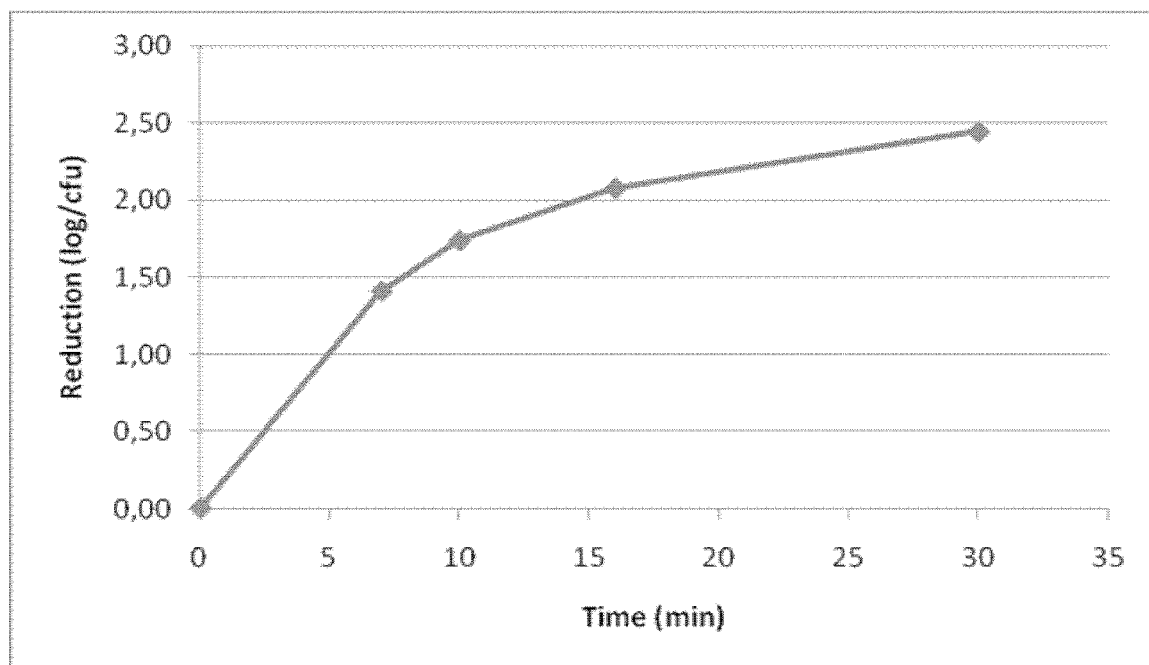
FIG. 5 shows the survival of spores in 100% chloroform in function of time.

Experiments showed that a 10 min treatment of 100% chloroform gave a reduction of maximum 1.7 log reduction in spore counts (FIG. 5).

Extracted spores migrate rapidly to the water phase, keeping the contact time with chloroform to a minimum. It can herefrom be anticipated that the extraction process has a minimal effect on spore survival.

From the results in Table 3, it can be seen that the selected spores survive the high temperature and high pressure incorporation in a polymer matrix, allowing further use of these organisms after incorporation.

TABLE 3

Reduction of spores after incorporation in polyester

| Sample | Reduction (log cfu) | Stdev |
|---|---|---|
| Fermentation | 0.5 | 0.4 |

Example 5

Influence of Material Properties on the Oxygen Scavenging Activity of Incorporated Organisms Introduction Dry spore material was incorporated in different polymer materials. The polymers were chosen in a broad range of polarity (Table 2). The polarity of polyurethane (PU)>Polylactic acid (PLA).

The polarity of a polymer has a great effect on the polymer moisture absorption. The more polar a polymer, the higher the uptake of water. This is demonstrated by the water absorption data for the several polymers (Table 2).

Material and Methods

Dry spore powder was produced by a suitable fermentation process and downstream processing. Dry spores were incorporated in two different polymers (PU and PLA) in 4% w/w concentration. Incorporation in the polymer matrix was done with a polymer press.

Plates of the polymer without spores (blanc) were pressed for 5 min at 130° C. for PU and 170° C. for PLA, at a pressure of 10 kN Dry spore powder was pressed in the correct concentration between two blanc polymer plates, allowing melt mixing of the spores within the polymer matrix to obtain one new mixed sample. Processing was done for 5 min at a temperature of 130° C. for PU and 170° C. for PLA and 10 kN.

The concentration of oxygen in the headspace was set to ±5% by flushing with nitrogen. 9 ml of sterile demineralised water was added to achieve the high humidity's needed for spores germination. To inhibit outgrowth of oxygen consuming micro-organisms in the water 10 mg/l ampicillin, a broad range antibiotic, was added. Oxygen absorption measurements were performed by placing 1.2 g of the pressed samples into a closed recipient with a headspace of 21 ml.

The oxygen concentration in the headspace was measured with a non invasive oxygen measurement device, the Oxysense 210T.

Results

The mean oxygen absorption rate (OAR) (ml $O_2$/day) was calculated over two repetitions. The data are given in Table 4.

TABLE 4

Oxygen absorption rate of spores incorporated in PU and PLA.

| Sample | OAR (ml/day) | Stdev |
|---|---|---|
| PU 4% 130° C. | 0.31 | 0.09 |
| PLA 4% 170° C. | 0.20 | 0.06 |

For the polymers PLA and PU (polarity value above 20), a good active oxygen scavenging activity could be noted. No significant difference between the oxygen absorption rate of PU and PLA could be observed.

From this experiment it can be concluded that when using a biological agent (spores) as active oxygen scavenger in a polymer those polymers can be used that are in compliance with our defined criteria regarding polarity and water absorption capacity.

REFERENCES

Biourge V, Vallet C, Levesque A, Sergheraert R, Chevalier S, Roberton J-L. The Use of Probiotics in the Diet of Dogs. J. Nutr. 1998; 128:2730S-2732S.

The invetion claimed is:

1. An apparatus comprising a beverage bottle or food container made of a material comprising a polymer and a micro-organism powder comprising living or viable spores of a micro-organism incorporated into said polymer and prepared by a process comprising mixing a polymer matrix comprising said polymer and said micro-organism powder at a pressure ranging from 1.5 to 50 bar or at temperatures ranging from 100° C. to 220° C. at a pressure ranging from 1.5 to 50 bar, wherein said micro-organism is a *Bacillus amyloliquefaciens* strain deposited under No. 1D9698 at the Belgian Co-ordinated Collections of Micro-organisms (BCCM), or a *Bacillus* strain with a gyrA sequence that is at least 95% identical to SEQ ID NO:1, and which is capable of withstanding a pressure ranging from 1.5 to 50 bar or at temperatures ranging from 100° C. to 220° C. at a pressure ranging from 1.5 to 50 bar, and wherein said polymer comprises at least one monomer selected from the group consisting of acrylates, methacrylates, acrylamides, methacrylamides, alcohols, amines, anhydrides, epoxides, styrenes, functionalized vinyls, functionalized allyls, propenes, butadienes, ethylenes, isocyanates, lactams, lactones, saccharides, glucose and esters.

2. The apparatus according to claim 1 acting as an oxygen barrier.

3. The apparatus according to claim 1, wherein said gyrA sequence is at least 98% identical to SEQ ID NO:1.

4. The apparatus according to claim 1, wherein said gyrA sequence is identical to SEQ ID NO:1.

5. The apparatus according to claim 1, wherein said micro-organism is the *Bacillus amyloliquefaciens* strain deposited under No. ID9698 at the Belgian Co-ordinated Collections of Micro-organisms (BCCM).

6. The apparatus of claim 3 acting as an oxygen barrier.

7. The apparatus of claim 5 acting as an oxygen barrier.

8. An apparatus comprising a beverage bottle or a food container made of a polymer and a micro-organism powder comprising living or viable spores of a micro-organism incorporated into said polymer and prepared by a process comprising mixing a polymer matrix comprising said polymer and said micro-organism powder at a pressure ranging from 1.5 to 50 bar or at temperatures ranging from 100° C. to 220° C. at a pressure ranging from 1.5 to 50 bar, wherein said micro-organism is a *Bacillus amyloliquefaciens* strain deposited under No. ID9698 at the Belgian Co-ordinated Collections of Micro-organisms (BCCM), or a *Bacillus* strain with a gyrA sequence that is at least 95% identical to SEQ ID NO:1, and which is capable of withstanding a pressure ranging from 1.5 to 50 bar or at temperatures ranging from 100° C. to 220° C. at a pressure ranging from 1.5 to 50 bar.

9. The apparatus of claim 8 acting as an oxygen barrier.

10. The apparatus according to claim 8, wherein said gyrA sequence is at least 98% identical to SEQ ID NO:1.

11. The apparatus according to claim 8, wherein said gyrA sequence is identical to SEQ ID NO:1.

12. The apparatus according to claim 8, wherein said micro-organism is the *Bacillus amyloliquefaciens* strain deposited under No. ID9698 at the Belgian Co-ordinated Collections of Micro-organisms (BCCM).

13. The apparatus according to claim 1, wherein the polymer has a polarity ranging from 17-21 $(MPa)^{1/2}$.

14. The apparatus according to claim 1, wherein the polymer has a minimal water absorption value selected from values of 0.01 to 0.1.

15. The apparatus according to claim 8, wherein the polymer has a polarity ranging from 17-21 $(MPa)^{1/2}$.

16. The apparatus according to claim 8, wherein the polymer has a minimal water absorption value selected from values of at least 0.01, 0.02, 0.1, or 0.2.

17. An apparatus comprising a food and beverage bottle or container made of material comprising a polymer and a micro-organism powder comprising living or viable spores of a micro-organism incorporated into said polymer in a polymer matrix having a polarity ranging from 17-21 $(MPa)^{1/2}$ and having minimal water absorption value ranging from of at least 0.01 to 0.2, wherein said apparatus is prepared by a process comprising mixing said polymer matrix and said micro-organism at pressure ranging from 1.5 to 50 bar or at temperatures ranging from 100° C. to 220° C. at a pressure ranging from 1.5 to 50 bar, wherein said micro-organism is a *Bacillus* strain with a gyrA sequence that is at least 95% identical to SEQ ID NO:1, and wherein said polymer comprises at least one monomer selected from the group consisting of acrylates, methacrylates, acrylamides, methacrylamides, alcohols, amines, anhydrides, epoxides, styrenes, functionalized vinyls, functionalized allyls, propenes, butadienes, ethylenes, isocyanates, lactams, lactones, saccharides, glucose and esters.

18. The apparatus according to claim 17, wherein the bottles and containers have a carbon dioxide barrier, wherein said micro-organisms consume of the bottles and containers carbon dioxide, or alternatively produce carbon dioxide that desorbs in content or acts as an osmotic barrier, wherein said micro-organisms are rehydrated, by using said polymer which is able to become water-saturated, to become sufficiently hydrated so that the living and viable spores therein are enabled to increase their water content and revert to metabolically active micro-organisms; wherein a polymer having a sufficiently high water absorption value is used; wherein the $H_2O$ absorption value of the polymer is at least 0.01; at least 0.02; at least 0.1 or at least 0.2.

19. The apparatus of claim 17 comprising a bottle made of polyethylene terephthalate (PET), wherein said micro-organisms are incorporated into the bottle an oxygen barrier.

20. The apparatus according to claim 17, wherein said gyrA sequence is at least 98% identical to SEQ ID NO:1.

21. The apparatus according to claim 17, wherein said gyrA sequence is identical to SEQ ID NO:1.

* * * * *

SEQUENCE LISTING

<160> NUMBER OF SEQ ID NOS: 1

<210> SEQ ID NO 1
<211> LENGTH: 773
<212> TYPE: DNA
<213> ORGANISM: Bacillus amyloliquefaciens

<400> SEQUENCE: 1

```
aaaaaatctg cccgtatcgt cggtgaagtt atcggtaagt accacccgca cggtgactca        60
gcggtttacg aatcaatggt cagaatggcg caggatttta actaccgcta catgcttgtt       120
gacggacacg gcaacttcgg ttcggttgac ggcgactcag cggccgcgat gcgttacaca       180
gaagcgagaa tgtcaaaaat cgcaatggaa attctgcgtg acattacgaa agacacgatt       240
gactatcaag ataactatga cggttcagaa agagaacctg ccgtcatgcc ttcgagattt       300
ccgaatctgc tcgtaaacgg ggctgccggt attgcggtcg gaatggcgac aaacattcct       360
ccgcatcagc ttggagaagt cattgaaggc gtgcttgccg taagtgagaa tcctgagatt       420
acaaaccagg agctgatgga atacatcccg ggcccggatt ttccgactgc tggtcagatt       480
ttgggccgga gcggcatccg caaggcatat gaatccggac ggggatcaat cacaatccgg       540
gctaaggctg aaatcgaaga gacatcatca ggaaaagaaa gaattattgt tacggaactt       600
ccttatcagg tgaacaaagc gagattaatt gaaaaaatcg cagatcttgt ccgggacaaa       660
aaaatcgaag gaattaccga cctgcgagac gaatccgacc gtaacggaat gagaatcgtc       720
attgagatcc gccgtgacgc cmatgctcac gtcattttga ataacctgta caa              773
```